(12) United States Patent
Broun

(10) Patent No.: US 6,835,540 B2
(45) Date of Patent: Dec. 28, 2004

(54) BIOSYNTHETIC PATHWAY TRANSCRIPTION FACTORS

(75) Inventor: Pierre Broun, San Mateo, CA (US)

(73) Assignee: Mendel Biotechnology, Inc., Hayward, CA (US)

(*) Notice: Subject to any disclaimer, the term of this patent is extended or adjusted under 35 U.S.C. 154(b) by 135 days.

(21) Appl. No.: 09/810,836

(22) Filed: Mar. 16, 2001

(65) Prior Publication Data

US 2002/0142281 A1 Oct. 3, 2002

(51) Int. Cl.$^7$ ............................ C12Q 1/68; C12N 15/82
(52) U.S. Cl. .......................... 435/6; 435/440; 435/468; 536/23.1; 536/24.1
(58) Field of Search ............................... 435/440, 468, 435/6; 536/23.1, 24.1

(56) References Cited

U.S. PATENT DOCUMENTS

| | | | | |
|---|---|---|---|---|
| 5,610,015 A | * | 3/1997 | Wickens et al. | ............... 435/6 |
| 5,928,888 A | | 7/1999 | Whitney | |
| 2003/0170656 A1 | * | 9/2003 | Cen et al. | ...................... 435/6 |

FOREIGN PATENT DOCUMENTS

| WO | WO 00/46383 | * | 8/2000 |
|---|---|---|---|

OTHER PUBLICATIONS

Liu et al. Two transcription factors, DREB1 and DREB2, with an ERBP/AP2 DNA binding domian separate two cellular transduction pathways in drought– and low–temperature–responsive gene expression,respectively, in Arabidopsis. Aug. 1998 Plant Cell 10: 1391–1406.*
Kim et al. The Plant Journal 11(6):1237–1251 1997.*
Riechman and Meyerowitz, Biol. Chem., Jun. 1998, vol. 379, pp 633–646.
Martin and Paz–Ares Trends in Genetics, Feb. 1997, vol. 13, pp 67–73.
Riechman and Meyerowitz, Biol. Chem., Oct. 1997, vol. 378, pp 1079–1101.
Ishiguro and Nakamura, Mol. Gen. Genet., 1994, vol. 244, pp 563–571.
Zhang et al., The Plant Cell, Dec. 1992, vol. 4, pp 1575–1588.
Kim et al., The Plant Journal, 1997, vol. 11, pp 1237–1251.
Klug and Schwabe, The FASEB J., May 1995, vol. 9, pp 597–604.
Burglin, in Guidebook to the Homeobox Genes (Editor, Duboule), pp II–V, 27–71, OUP, Oxford, U,K. 1996.
Forsburg and Guarante, Genes and Development, 1989 vol. 3, pp. 1166–1178.
Klein et al, Mol. Gen. Genet, 1996 vol. 250, pp 7–16.
Rouse et al, Science, Feb. 27, 1998 vol. 279, pp 1371–1373.
Tucker et al, The EMBO J., 1994 vol. 13, pp 2994–3002.
Foster et al, The FASEB J., Feb. 1994 vol. 8, pp 192–200.
da Costa eSiNa et al., The Plant Journal, 1993 vol. 4, pp 125–135.
Hall et al., The Plant Cell, Jun 1998 vol. 10, pp. 925–936.
Yamaguchi–Shinozaki and Shinozaki, Mol Gen Genet, 1993, vol 236, pp. 331–340.
Gilmour et al, The Plant Journal, 1998 vol. 16, pp. 433–442.
Riechmann et al, Science, Dec. 15, 2000 vol. 290, pp 2105–2110.

* cited by examiner

*Primary Examiner*—James Ketter
*Assistant Examiner*—David A. Lambertson
(74) *Attorney, Agent, or Firm*—Jeffrey M. Libby; Matthew R. Kaser

(57) ABSTRACT

The present invention provides a high-throughput method for identifying a polynucleotide which encodes a transcription factor for controlling the expression of one or more genes in a pathway. In particular, the method is useful for identifying a transcription factor for controlling a gene in a biosynthetic pathway. The invention further provides polynucleotides encoding such transcription factors for controlling the expression of a gene in a biosynthetic pathway, transgenic cells expressing at least one such polynucleotide, and methods for isolating metabolites from such cells or plants.

29 Claims, No Drawings

BIOSYNTHETIC PATHWAY TRANSCRIPTION FACTORS

BACKGROUND OF THE INVENTION

Cells synthesize both primary and secondary metabolites. Primary metabolites are necessary for basal growth and maintenance of the cell and include certain nucleic acids, amino acids, proteins, fats, and carbohydrates. In contrast, secondary metabolites are not necessary for basal function, but often confer highly desirable traits to an organism. These metabolites are a chemically diverse group of compounds that includes alkaloid compounds (e.g., terpenoid indole alkaloids and indole alkaloids), phenolic compounds (e.g., quinones, lignans and flavonoids), and terpenoid compounds (e.g. monoterpenoids, iridoids, sesquiterpenoids, diterpenoids and triterpenoids).

Plant secondary metabolites have great value as pharmaceuticals, food colors, flavors and fragrances. Plant pharmaceuticals include taxol, digoxin, colchicine, codeine, morphine, quinine, shikonin, ajmalicine and vinblastine. Examples of secondary metabolites that are useful as food additives include anthocyanins, vanillin, and a wide variety of other fruit and vegetable flavors and texture modifying agents. In addition, some plant secondary metabolites are part of the plant's defense system, conferring protection against UV light, herbivores, pathogens, microbes, insects and nematodes, as well as the ability to grow at low light intensity.

A particularly valuable secondary metabolite class is the terpenoid class. Plant terpenoids represent a very diverse class of chemicals, comprising about 30,000 different molecules. They play a central role in plant biology, for example, in defense against pathogens and herbivores, and in attracting pollinators. Their physical and chemical properties are quite diverse. Terpenoids range from large polymers such as rubber to small volatile molecules such as menthol, and include many valuable chemicals used to make medicines and fine chemicals. Alone, worldwide sales of plant terpenoid-derived drugs amount to over $10 billion yearly.

In many cases, a key limiting factor to commercial production of secondary metabolites is the rate at which plants synthesize them. Problematically, only very small or variable amounts of these compounds are present in plants. The recovery of useful metabolites from their natural sources is thus in many instances difficult due to the enormous amounts of source material that may be required for the isolation of utilizable quantities of the desired products. Extraction is both costly and tedious, requiring large quantities of raw material and extensive use of chromatographic fractionation procedures. homology to known transcription factors. By design, this screening method excludes identification of many potentially useful transcription factors, such as those structurally unrelated to transcription factors already implicated in biosynthetic pathways. Furthermore, this method does not identify transcription factors that act may act in combination, in particular, ones that may act synergistically to effect gene expression.

Therefore, there is a need for a high-throughput method to identify transcription factors that regulate metabolite biosynthesis in plants. A desirable approach would be to express a pool of transcription factors in cells and to measure the effect on expression of a biosynthetic pathway gene. This invention fulfills this and other needs.

SUMMARY OF INVENTION

In one aspect, the present invention provides a high-throughput method for determining whether a polynucleotide encodes a transcription factor for a pathway gene. The method entails determining whether a member of a pool of test transcription factor polynucleotides encodes a pathway transcription factor. A nucleic acid comprising a pathway gene promoter operably linked to a reporter gene and a pool of nucleic acid members comprising test transcription factor polynucleotides are introduced into a cell and expression from the pathway gene promoter in the cell is detected. Thereby it is determined whether a member of the test transcription factor polynucleotide pool encodes a pathway transcription factor.

The method can be also be used to allow for high-throughput screening for determining functional interactions between multiple test transcription factors and multiple pathway gene promoters simultaneously. Preferably, the methods of this invention are directed towards identification of transcription factors for genes in pathways relating to metabolite biosynthesis or environmental stresses (biotic or abiotic). With respect to metabolite biosynthesis, the invention is preferably directed to the pathway for the biosynthesis of terpenoids or alkaloids. Preferred terpenoids include, but are not limited to, monoterpenes, diterpenes, and sesquiterpenes. The genes from which promoters may be derived include, but are not limited to, genes from Nicotiana, Mentha, and Taxus. In addition, these genes include, but are not limited to, 5-epi-aristolochene synthase, limonene synthase, and taxadiene synthase.

In another embodiment, a pool of known or putative promoters may be screened. In another embodiment, polynucleotides encoding the test transcription factors are preferably expressed transiently in the plant cell by methods including, but not limited to, Agrobacterium-mediated expression. In yet another embodiment, the expression level of the pathway gene is determined using a promoter of the gene under study operably linked to a reporter gene, such as GUS. In a further embodiment, the expression level of the genes is determined indirectly by measurement of metabolite accumulation in a plant cell or a whole plant regenerated from a cell. In yet a further embodiment, the expression level is directly measured by quantitation of RNA levels in the plant cell or plant.

In a further embodiment, the method may further entail deconvoluting the pool of nucleic acid members to identify the minimum number of test transcription factor polynucleotides necessary to detect expression from said pathway gene promoter.

In another aspect, and if the method is employed to identify test transcription factors for a metabolite pathway, the method may entail introducing into a cell a pool of nucleic acid members comprising test transcription factor polynucleotides and detecting accumulation of metabolites, such as terpenoids, in the cell.

In yet another aspect, the present invention also comprises biosynthetic pathway transcription factors disclosed as SEQ ID NOs: 2, 4, 6, 8 and nucleic acids encoding them or related biosynthetic pathway transcription factors and a transgenic plant or plant cell comprising a nucleic acid encoding a pathway transcription factor identified by the methods provided.

Definitions

As used herein, the term "transcription factor" refers to any polypeptide that may act by itself or in combination with at least one other polypeptide to regulate gene expression levels and the term is not limited to polypeptides that directly bind DNA sequences. The transcription factor typically increases expression levels. However, in some cases it may be desirable to suppress expression of a particular pathway. The transcription factor may be a transcription factor identified by sequence analysis or a naturally-occuring reading frame sequence that has not been previously characterized as a transcription factor. The polypeptide may also be an artificially generated or chemically or enzymatically modified polypeptide. A given nucleic acid sequences may be modified, e.g., according to standard mutagenesis or artificial evolution or domain swapping methods to produce modified sequences. Accelerated evolution methods are described, e.g., by Stemmer (1994) *Nature* 370:389–391, and Stemmer (1994) *Proc. Natl. Acad. Sci. USA* 91:10747–10751. Chemical or enzymatic alteration of expressed nucleic acids and polypeptides can be performed by standard methods. For example, sequence can be modified by addition of phosphate groups, methyl groups, lipids, sugars, peptides, organic or inorganic compounds, by the inclusion of modified nucleotides or amino acids, or the like. Further the transcription factor may be derived from a collection of transcripts, such as a cDNA library, and the sequence of the transcript may be unknown.

The phrase "test transcription factor" refers to a polypeptide that is being tested for its ability to act as a transcription factor to regulate a pathway gene, for example, a biosynthetic pathway gene, an environmental (biotic or abiotic) stress gene or the like. Test transcription factors used in assays of this invention may be selected from a pool on the basis of structural similarity to known transcription factors for one or more pathways under investigation. Test transcription factors may also be selected based on their expression patterns in cells or plants that conform to when pathway genes are expressed. Test transcription factors may also be selected randomly or without bias.

As used herein, the term "pool" refers to a collection of transcription factors. The pool may comprise at least two transcription factors, at least three transcription factors, at least four transcription factors, at least 5 transcription factors and including additional one transcription factor increments up to 40, 80, 100, 500, 1000, 2000, 3000 or more transcription factors. The pool may be subdivided into subpools which are introduced into a single cell when the screening is performed. Preferably, any given subpool may comprise between 2 to 20 transcription factors, more preferably between 4 and 16 transcription factors. Therefore, if a total of 2000 transcription factors are screened and 4 transcription factors polynucleotides are transformed simultaneously into each cell (or subpool), then 500 cells would be tested for expression from at least one promoter.

The term "secondary metabolite" refers to any compound that is not essential to the basal function of a cell. Typical secondary metabolites include alkaloid compounds, phenolic compounds, and terpenoid compounds.

A "polynucleotide" is a nucleic acid sequence comprising a plurality of polymerized nucleotide residues, e.g., at least about 15 consecutive polymerized nucleotide residues, optionally at least about 30 consecutive nucleotides, at least about 50 consecutive nucleotides. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

The term "promoter" refers to regions or sequence located upstream and/or downstream from the start of transcription and which are involved in recognition and binding of RNA polymerase and other proteins to initiate transcription. The promoter may be of a known or unknown sequence and may be known to drive expression of a particular gene or may be a putative promoter. A "plant promoter" is a promoter capable of initiating transcription in plant cells.

The term "cell" refers to a cell from any organism, including plants, bacteria, fungi or animals The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae.

The phrase "structural similarity" refers to a polynucleotide or polypeptide having a minimal level of sequence identity to another polynucleotide or polypeptide. The minimal level of sequence identity may be as low as 20% to 30% over any segment of a sequence.

A "transiently transfected" cell expresses a desired polynucleotide, but only for a limited period of time.

The term "high-value secondary metabolites" refers to those secondary metabolites that have valuable commercial applications.

As used herein, the term "transgenic" refers to a plant cell or plant where a nonendogenous nucleic acid has been introduced into the plant by any means. Examples of means by which this can be accomplished are described below, and include Agrobacterium-mediated transformation, biolistic methods, electroporation, and the like.

BRIEF DESCRIPTION OF SEQUENCE IDENTIFIERS

SEQ ID NO: 1 is the polynucleotide sequence of G993, a clone that activates transcription of the taxadiene synthase gene. SEQ ID NO: 2 is the corresponding polypeptide.

SEQ ID NO: 3 is the polynucleotide sequence of G1845, a clone that activates transcription of the taxadiene synthase gene. SEQ ID NO: 4 is the corresponding polypeptide.

SEQ ID NO: 5 is the polynucleotide sequence of G1386, a clone that activates transcription of the taxadiene synthase gene or the limonene synthase gene. SEQ ID NO: 6 is the corresponding polypeptide.

SEQ ID NO: 7 is the polynucleotide sequence of G872, a clone that activates transcription of the taxadiene synthase gene. SEQ ID NO: 8 is the corresponding polypeptide.

DETAILED DESCRIPTION OF EMBODIMENTS

The present invention is directed towards a method for the identification of one or more transcription factors that activate one or more genes of a biological pathway. The biological pathway can be a biochemical pathway (such as biosynthetic pathways for amino acids, soluble and insoluble carbohydrates, proteins, lipids, terpenoids, chlorophylls, phenylpropanoids, vitamins and cofactors, nucleic acids, alkaloids, tannins, miscellaneous secondary metabolites, or corresponding degradation pathways); a response pathway to abiotic stress (such as freezing, cold, drought, heat, nutrient deficiency, pH, anoxia, heavy metal, or oxidative stress) or biotic stress (such as disease, fungal, viral, bacterial, herbivory, wounding, or parasitism); a developmental pathway (such as flowering, root development, development of vegetative tissue, or seed development); a response pathway to environmental cues (such as light intensity and light quality, circadian rhythm, gravity, sound, touch, oxygen, carbon dioxide levels, or humidity).

In one aspect, the method entails determining whether a member of a pool of test transcription factor polynucleotides encodes a pathway transcription factor. A nucleic acid comprising a pathway gene promoter operably linked to a reporter gene and a pool of nucleic acid members comprising test transcription factor polynucleotides are introduced into a cell and expression from the pathway gene promoter in the cell is detected. Thereby it is determined whether a member of the test transcription factor polynucleotide pool encodes a pathway transcription factor that induces expression from the pathway gene promoter. In some instances, it may be useful to deconvolute the pool of nucleic acid members to identify whether single transcription factors or transcription factor combinations are for expression.

One of skill in the art will recognize that the particular pathway gene promoter examined in the method of this invention is not critical. Promoters of choice include, but are not limited to, those of genes encoding branch-point enzymes that are transcriptionally regulated. Examples of branchpoint enzymes include, in the case of amino acid biosynthesis, 3-deoxy-D-arabino-heptulosonate 7-phosphate synthase, anthranilate synthase and chorismate mutase (for the synthesis of aromatic amino acids), asparagine synthase, aspartate aminotransferase (for the synthesis of asparagine and aspartate respectively), glutamate synthase (for the synthesis of glutamate), aspartate kinase, dihydrodipicolinate synthase and homoserine dehydrogenase (for the synthesis of lysine, threonine and isoleucine), methionine synthase, acetohydroxy acid synthase (leucine and valine biosynthesis), threonine deaminase (isoleucine pathway), and delta-1 pyrroline-5-carboxylate synthetase (proline biosynthesis).

Other promoters for genes of interest include the following. For seed storage proteins, genes of interest include those encoding napin, zein, and vegetative storage protein. Examples of genes involved in the production of soluble sugars and starch include those encoding sucrose phosphate synthase, sucrose phosphate synthase phosphatase, starch synthases, invertase, sucrose synthase, starch branching enzymes, and hexokinase. Enzymes of the starch degradation pathway include starch phosphorylase, debranching enzymes, beta-amylase, alpha-glucosidase. In the case of cell-wall biosynthesis, cellulose synthase-like enzymes, UDP-glucose pyrophosphorylase, and GDP-glucose pyrophosphorylase are genes of interest. Lipid biosynthesis genes of choice encode acetyl-CoA carboxylase, ketoacyl-ACP synthases, thioesterases, fatty acid desaturases, glycerol-3-phosphate acyltransferase, lysophosphatidate acyltransferase, and diacylglycerol acyltransferase. Preferred degradation enzymes include malate synthase, isocitrate lyase, and acyl-CoA oxidase. Identification of transcription factors controlling the phenylpropanoid pathway can involve study of genes encoding phenylalanine ammonia lyase, cinnamate4 hydroxylase, p-coumaric acid (or coumaroyl-CoA) hydroxylase, chalcone synthase for the production of flavonoids, stilbene synthase for the production of stilbenes, CoA ligases, caffeic acid, ferulic acid, hydroxy-ferrulic acid, sinapic acid, and the O-methyltransferases of the resulting CoA esters, for the production of lignins and lignans.

Genes involved in secondary metabolite production include those of taxa-4(20),11(12)-dien-5alpha-ol-O-acetyltransferase for the production of taxol; tyrosine decarboxylase, (S)-norcoclaurine synthase, 3'-hydroxy-N-methylcoclaurine 4'-O-methyltransferase, and berberine bridge enzymes for the production of tetrahydrobenzylisoquinoline alkaloids; anthranilate synthase, strictosidine synthase, tryptophan decarboxylase D-1-deoxyxylulose 5-phosphate synthase, geraniol 10-hydroxylase, strictosidine -D-glucosidase, desacetoxyvindoline 4-hydroxylase, acetyl-CoA:4-O-deacetylvindoline 4-0-acetyltransferase and other enzymes for the production of terpene indole alkaloids; HMG-CoA synthase, squalene synthase and squalene epoxidase for the production of terpenoids; geranylgeranyl diphosphate synthase and diterpene cyclases (such as taxadiene synthase and casbene synthase) for the synthesis of sterols and other triterpenes; farnesyldiphosphate synthase for the production of diterpenes; sesquiterpene synthases such as 5-epi-aristolochene synthase for the production of sesquiterpenes, geranyldiphosphate synthase and monoterpene cyclases (such as limonene synthase) for the production of monoterpenes, and phytoene synthase for the production of tetraterpenes such as carotenoids. Also, the genes may encode a polypeptide that catalyzes a rate-limiting step in a biosynthetic pathway.

Examples of genes involved in cold response are those of the COR genes (such as Arabidopsis COR15); in drought response, Arabidopsis RD29B; in salt response ENA1/PMR2A; in osmotic stress, GPD1; in heat stress, HSP genes; in nutrient deficiency, nitrate reductase (for nitrates), PAP1 (for phosphates), and Arabidopsis AKT genes (potassium); in oxidative stress, ascorbate peroxidase or glutathione reductase; in heavy metal response, phytochelatin synthase. Examples of genes for response to pathogens are those of PR1 and PDF1.2 and for response to wounding, 1-aminocyclopropane-1-carboxylate synthase from apples or agropine synthase. Genes of interest in developmental pathways include the following genes: LEAFY for flowering, AINTEGUMENTA for leaf development, LEC1 for embryo formation, CAB genes for light intensity and circadian rhythm, CHS genes for light quality, for gravity, and TCH genes for touch.

The test transcription factors and the pathway gene promoters may be derived from any cell, but are preferably derived from plants including monocots and dicots including but not limited to, crops such as soybean, wheat, corn, potato, cotton, rice, oilseed rape (including canola), sunflower, alfalfa, sugarcane and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, spinach, squash, sweet corn, mint, tobacco, tomato, watermelon, rosaceous fruits (such as apple, peach, pear, cherry and plum) and vegetable brassicas (such as broccoli, cabbage, cauliflower, brussel sprouts and kohlrabi). Other crops, fruits and vegetables whose phenotype can be changed include barley, rye, millet, sorghum, currant, avocado, citrus fruits such as oranges, lemons, grapefruit and tangerines, artichoke, cherries, nuts such as the walnut and peanut, endive, leek, roots, such as arrowroot, beet, cassava, turnip, radish, yam, and sweet potato, and beans.

The homologous sequences may also be derived from woody species, such pine, poplar, yew and eucalyptus.

The following description focuses on identification of transcription factors acting on metabolite pathway genes. However, one of skill in art will readily recognize that the methods of the invention can also be applied to genes including, but not limited to, those described above.

Secondary Metabolites of the Invention

The method of this invention identifies one or more transcription factors which increase the expression level of secondary metabolite genes, the biosynthetic rate of plant secondary metabolites, and/or the level of plant secondary metabolites by any significant percentage, but preferably, at least 10%, at least 20%, at least 50%, at least 100% or 200%, at least 300% or 500%, a least 700% or 1000%. Secondary metabolites to be examined in the method of this invention include, but are not limited to, alkaloid compounds, phenolic compounds (e.g., quinones, lignans and flavonoids), and terpenoid compounds (e.g., monoterpenoids, iridoids, sesquiterpenoids, diterpenoids and triterpenoids). In one embodiment, the secondary metabolite is an alkaloid compound or a terpenoid compound. The alkaloid can be a terpenoid indole alkaloid, an indole alkaloid, nicotine, morphine, capsaicin, caffeine, quinine, etc. Preferably, the terpenoid is a monoterpene, sesquiterpene, or a diterpene. Pathway genes of secondary metabolites suitable for screening can be identified by scanning published literature on secondary metabolite-producing plants to identify genes whose sequence and expression profile is known.

It will be readily recognized by one of skill in the art that the particular plant secondary metabolite gene examined in the method of this invention is not critical. In one embodiment, endogenous terpenoid pathway genes of Mentha, tobacco, and Taxus are examined. Peppermint accumulates essential oil (1–2% dw) that consists almost exclusively of monoterpenes, such as menthol and menthone. The first committed step into the pathway is the synthesis of the cyclic molecule limonene. The limonene synthase gene is expressed in leucoplasts of trichome secretory cells, and its expression coincides with the expression of other genes in the pa way. The promoter for the limonene synthase gene was identified and sequenced as described in U.S. patent application Ser. No. 09/699.083. filed Oct. 27. 2000. now abandoned.

Tobacco produces sesquiterpene phytoalexins in response to fungal elicitors. The main sesquiterpene produced is capsidiol. The elicitor-induced accumulation of capsidiol correlates with the induction of 5-epi-aristolochene synthase, which is considered the branch point into sesquiterpene phytoalexin production in tobacco, eas genes constitute a 12–15 member strong gene family in tobacco. The promoter of one of the gene members, eas4, has been characterized in detail. Expression of eas4 (and activity of its promoter) matches closely 5-epi-aristolochene synthase activity and fairly closely capsidiol accumulation in elicited tobacco cell suspension cultures.

Certain Taxus species accumulate paclitaxel, which consists of a diterpene moiety and a benzoyl phenylisoserine moiety. Taxadiene synthase catalyzes the first committed step into biosynthesis of the terpenoid moiety of the paclitaxel molecule. The fact that paclitaxel production does not significantly increase when cell suspension cultures are supplemented with phenylalanine, a precursor of the phenylpropanoid moiety, suggests that this pathway is not limiting to Paclitaxel accumulation. In contrast, addition of jasmonate, which induces enzymes of the diterpenoid pathway, greatly increases paclitaxel accumulation in cell culture. This suggests that synthesis and modification of the taxane ring is limiting to paclitaxel accumulation. Taxadiene synthase catalyzes the first step into the taxane biosynthesis pathway. The gene is jasmonate-inducible, and its induction correlates with the onset of paclitaxel accumulation. The promoter for the taxadiene synthase gene was identified and sequenced as described in U.S. patent application Ser. No. 09/699,083, filed Oct. 27, 2000, now abandoned.

Plant Cell Tissue Culture

The method of this invention may be performed in in vitro plant cell cultures.

In one embodiment, plant cultures used in the method of this invention are from Arabidopsis. Advantageously, Arabidopsis is an extremely well developed model system and furthermore, the complete genome is available. Alternatively, cultures can be from any species of plant which expresses high-value secondary metabolites. Preferably, the cultures are from plants that accumulate secondary metabolites in cell culture.

Suspension plant cultures that produce high-value terpenoids include *Piqueria trinervia,* a member of the Asteraceae family, which produces monoterpenes in response to elicitors; Tobacco, which produces the sesquiterpene capsidiol in response to fungal elicitors; Cotton, which produces sesquiterpene derivatives, such as sesquiterpene aldehyde gossypol in response to fungal elicitors; Rice, which accumulates diterpene phytoalexins, such as momilactone and a number of oryzalexins; *Gingko biloba,* which produces diterpenes such as gingkolide and bilobalides, and Taxus species, which produce a variety of taxoids. If desired, the method of this invention may also be conducted in other plant species which may produce high-value secondary metabolites under certain conditions.

Callus or cell cultures are obtained, when possible, from academic laboratories and public collections. Alternatively, published protocols may be followed to establish in-house cell cultures for the different species. Typically, explants provide a source of callus that can be used to inoculate liquid cultures. After several transfers and selection for small aggregates, cell cultures can then be scaled up in order to obtain the desired volumes needed for screening and Agrobacterium infection. Cell cultures are maintained according to basic protocols described in Evans et al., *Handbook of Plant Cell Culture,* Macmillan Publishing Company, New York, 1983. Culture conditions, such as certain elicitors or inducers, can be optimized to allow plant cells to produce the maximum amount of secondary metabolites. Published protocols for the extraction and analysis of cell cultures can be applied. Multiple cultures can be harvested over a period of time to determine the normal variability of secondary metabolite accumulation in the presence or the absence of inducers.

Transcription Factors of the Invention

The method of this invention comprises determining whether test transcription factors increase expression levels of certain secondary metabolite pathway genes and whether these transcription factors increase biosynthetic rates and/or levels of secondary metabolites. These transcription factors may be from any known plant species but are preferably from Arabidopsis. Pools of more than one transcription factor can be examined in the method of this invention. Members of these pools can be selected on the basis of structural similarity to known transcription factors including, but not limited to, those described below. Alternatively, members of these pools are selected without regard to structural similarity to known transcription factors. The transcription factors may be generated artificially or be chemically or enzymatically modified prior to screening. Further, the transcription factors may be of unknown or incomplete sequence.

The transcription factors, if the sequence is known, may belong, e.g., to one or more of the following transcription factor families: the AP2 (APETALA2) domain transcription factor family (Riechmann and Meyerowitz (1998) *J. Biol. Chem.* 379:633–646); the MYB transcription factor family (Martin and Paz-Ares (1997) *Trends Genet.* 13:67–73); the MADS domain transcription factor family (Riechmann and Meyerowitz (1997) *J. Biol. Chem.* 378:1079–1101); the WRKY protein family (Ishiguro and Nakamura (1994) *Mol. Gen. Genet.* 244:563–571); the ankyrin-repeat protein family (Zhang et al. (1992) *Plant Cell* 4:1575–1588); the miscellaneous protein (MISC) family (Kim et al. (1997) *Plant J.* 11:1237–1251); the zinc finger protein (Z) family (Klug and Schwabe (1995) *FASEB J.* 9: 597–604); the homeobox (HB) protein family (Duboule (1994) *Guidebook to the Homeobox Genes,* Oxford University Press); the CAAT-element binding proteins (Forsburg and Guarente (1989) *Genes Dev.* 3:1166–1178); the squamosa promoter binding proteins (SPB) (Klein et al. (1996) *Mol. Gen. Genet.* 1996 250:7–16); the NAM protein family; the IAA/AUX proteins (Rouse et al. (1998) *Science* 279:1371–1373); the HLH/MYC protein family (Littlewood et al. (1994) *Prot. Profile* 1:639–709); the DNA-binding protein (DBP) family (Tucker et al. (1994) *EMBO J.* 13:2994–3002); the bZIP family of transcription factors (Foster et al. (1994) *FASEB J.* 8:192–200); the BPF-1 protein (Box P-binding factor) family (da Costa e Silva et al. (1993) *Plant J.* 4:125-135) golden protein (GLD) family (Hall et al. (1998) *Plant Cell* 10:925–936).

We have do ed Arabidopsis transcription factors and generated stable overexpressing lines for over 600 transcriptia factors for use in the method of the invention. These Arabidopsis transcription factor sequences and ethods for identifying other putative transcription factor sequences are described in U.S. pat. app. Ser. Nos. 09/394,5 19, filed Sep. 13. 1999. now abandoned, 09/506,720, filed Feb. 17. 2000. now abandoned, 09/533,030, filed Mar. 22. 2000. now abandoned, 09/533,392, filed Mar. 22. 2000. now abandoned, 09/533,029, filed Mar. 22. 2000. pending, 09/532,591, filed Mar. 22, 2000, now abandone 09/533,648, filed Mar. 22, 2000, now abandoned, or PCT publications PCT/US00/31418 filed Nov. 14, 2000, now expired, PCT/US00/31458, filed Nov. 14, 2000, now expired, PGT/US00/31457, filed Nov. 14, 2000, now expired, PCT/US00/31325, filed Nov. 14, 2000, now expire , PCT/US00/31414, filed Nov. 14, 2000, now expired, PCT/US00/31344, filed Nov. 14, 2000, ow exnired, and PGT/US00128141. filed Oct. 11, 2000, now expired.

Construction of Vectors for Introduction into Plant Cells

The method of this invention comprises introducing into a plant cell a nucleic acid comprising a potential transcription factor for a metabolite pathway gene. In certain preferred embodiments, the method also comprises introducing into the plant cell a vector encoding a promoter of a metabolite gene-reporter construct or a metabolite pathway gene of another species. These vectors can be constructed by any method known to those of skill in the art as described in Maniatis et al., or as described below.

To produce cells overexpressing exogenous DNA sequences, recombinant DNA vectors suitable for transformation of plant cells are prepared. In general, a DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumafaciens,* the figwort mosaic virus promoter, and other transcription initiation regions from various plant genes.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Transformation of Plant Cells

These vectors can be introduced into plant cell cultures by any method known to those of skill in the art to establish transient or stable overexpressing cells. Techniques for transforming a wide variety of higher plant species are well known and described in the technical and scientific literature. See, for example, Weising et al. *Ann. Rev. Genet* 22:421–477 (1988). Methods are known for introduction and expression of heterologous genes in both monocot and dicot plants. See, e.g., U.S. Pat. Nos. 5,633,446, 5,317,096, 5,689,052, 5,159,135, and 5,679,558. For a review of gene transfer methods for plant and cell cultures, see, Fisk et al., *Scientia Horticulturae* 55:5–36 (1993) and Potrykus, *CIBA Found. Symp.* 154:198 (1990).

Cells can be transiently transfected via carrier-mediated transfection of protoplasts, including microinjection and electroporation. Electroporation techniques are described in Fromm et al. *Proc. Natl. Acad. Sci. USA* 82:5824 (1985). Preferably, these techniques can occur via treatments with polycations and/or charged liposomes but most preferably, via polyethylene glycol (PEG) treatments. The introduction of DNA constructs using polyethylene glycol precipitation is described in Paszkowski et al. *EMBO J.* 3:2717–2722 (1984).

In a preferred embodiment, Agrobacterium infiltration of whole plants (in planta) is used to generate transiently transfected cells. Preferred plant species for infiltration include *N. benthamiana* and preferred Agrobacterium strains for infiltration are nopaline strain C58C1, derivatives ABI and GV3101, and agropine/succinamopine strains A281. The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al.

*Proc. Natl. Acad. Sci. USA* 80:4803 (1983) and *Gene Transfer to Plants,* Potrykus, ed. (Springer-Verlag, Berlin 1995). Preferred techniques include transformation using electroporation or triparental mating with binary vectors.

In yet another embodiment, Agrobacterium is used to mediate transcription factor expression in cell suspension cultures. The protocol from the Koncz lab (Ferrando et al. 2000) may be used. ABI is the preferred Agrobacterium strain for this method.

In still yet another embodiment, ballistic methods, such as DNA particle bombardment will be used for plant leaves. Ballistic transformation techniques are described in Klein et al. *Nature* 327:70–73 (1987). Particle-mediated transformation techniques (also known as "biolistics") are described in, e.g., Klein et al., *Nature,* 327:70–73 (1987); Vasil, V. et al., *Bio/Technol.* 11:1553–1558 (1993); and Becker, D. et al., *Plant J.,* 5:299–307 (1994). These methods involve penetration of cells by small particles with the nucleic acid either within the matrix of small beads or particles, or on the surface. The biolistic PDS-1000 Gene Gun (Biorad, Hercules, Calif.) uses helium pressure to accelerate DNA-coated gold or tungsten microcarriers toward target cells. The process is applicable to a wide range of tissues and cells from organisms, including plants, bacteria, fungi, algae, intact animal tissues, tissue culture cells, and animal embryos.

General Methods for Examining the Effect of Putative Transcription Factors on Secondary Metabolite Levels The method of this invention typically identifies transcription factors that increase plant production of secondary metabolites. However, in some cases, it may be desirable to decrease production levels. Production levels can be measured by any method known to those of skill in the art. Methods can either measure levels of gene expression or accumulation of the secondary metabolite itself. In one embodiment of this invention, transcription factors are identified by directly measuring activation of secondary metabolite promoters with an attached reporter gene. In another embodiment, activity of secondary metabolite genes under study are examined by measuring secondary metabolite levels. In yet another embodiment, mRNA levels are quantitated.

Secondary Metabolite Promoter/ Reporter Gene Constructs

As described above, in one embodiment transcription factors which increase the biosynthetic rate of secondary metabolites are identified by directly measuring activation of secondary metabolite promoters with an attached reporter gene.

The reporter gene can be any reporter used by those of skill in the art. Commonly used reporters include green fluorescent protein (GFP), luciferase, anthocyanin, and chloramphenicol acetyltransferase (CAT). Int-GUS (uidA containing an intron from a potato gene) is the preferred reporter for transient assays, since gene expression can be measured quantitatively even at very low levels, and the protein product is not functional in Agrobacterium. This last property is desirable for accurate measurements in the case of Agrobacterium-mediated transformation.

One of skill in the art will readily recognize that promoters from any plant species can be examined in any plant species of interest. However, promoters are preferably from species that produce high-value terpenoids and examined for example in Arabidopsis cells or other plant cells.

Promoters of metabolite pathway genes can be readily identified from the literature or by scanning public plant genome sequence database, although it may be necessary in certain cases to first identify the boundaries of the coding region experimentally. In one embodiment, the coding region of a metabolite pathway genes is defined either by sequence alignment to known genes in other species, or experimentally by 5' RACE. Sequences upstream of the coding region are identified by inspection of the genomic sequence and cloned into a reporter-expressing expression vector. The promoter sequences may be of any length necessary to elicit transcription of a gene. The sequences may be as short as 8 nucleotides or as long as 5 to 7 kilobases. Preferably the promoter sequences are between 200 and 2000 nucleotides long.

For some metabolite genes from other species, no genomic sequence may be available. In this case it may be necessary to isolate promoter sequences from genomic DNA using appropriate techniques. Genomic DNAs are obtained and promoter sequences can be PCR-amplified using primers designed after their published sequence. The promoter fragments can be cloned into a plant expression vector upstream of a reporter gene. In another embodiment, promoters are cloned as follows. Adaptors are ligated to genomic fragments from target high-secondary metabolite species. Promoter sequences are amplified using gene-specific primers and adaptor primers. 1-2 kb fragments are end-sequenced and used to design promoter-specific primers. Promoter fragments are amplified and cloned into a reporter-containing expression vector.

Controls can be conducted to determine if the isolated promoter sequences confer on the reporter gene an expression pattern that is relevant to expression of the native gene and to establish whether these secondary metabolite promoters are active in for example Arabidopsis. When the reporter constructs are transfected into plant cells, the basal level of reporter gene activity is measured as a control.

Regeneration of Plants

In certain embodiments of methods of this invention, whole plants, rather plant cells are examined. Plant cells can easily be cultured to regenerate a whole plant by any method known to those of skill in the art. In general, such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture,* pp. 124–176, Macmillan Publishing Company, New York, 1983; and Binding, *Regeneration of Plants, Plant Protoplasts,* pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

Biochemical Analysis of Cell Culture or Plants

In a second preferred embodiment of the screening method of this invention, transcription factors which increase secondary metabolite biosynthesis are identified by biochemical analysis of cell cultures or whole plants. Advantageously, this method directly addresses the effects of transcription factors on secondary metabolite accumulation, rather than the effect on individual pathway genes. Secondary metabolites are extracted from flowers and leaves of plants or plant cell culture. Metabolites can be quantitated by any method known to those of skill in the art, such as GC-MS or HPLC (Satterwhite et al. *J Chromatogr.* 452:61–73 (1988)).

Screening Multiple Transcription Factors and Multiple Promoters

In one embodiment of the method where promoter-reporter genes are employed, multiple transcription factors and multiple metabolite gene promoters are assayed at the same time by any method that allows for high-throughput screening of compounds for activity. Assaying several transcription factors simultaneously allows for rapid identification of transcription factor combinations that activate a single gene or multiple genes. In particular, this method is useful for identifying transcription factors which act synergistically and have no or little activity unless in combination with other transcription factors. Typically, at least four; more preferably, eight; even more preferably, sixteen; and most preferably, 20 transcription factors are assayed simultaneously in a single cell for their effect on gene expression. Typically, as the number of transcription factors increases, the amount of each individual transcription factor decreases. As shown below, less than half of the typical amount of DNA used for transfection is effective for enhancing transcription of secondary metabolite pathway genes under investigation. As described in the examples, a little as $\frac{1}{16}$ of the typical amount of DNA enhances transcription of a pathway gene by 12-fold. Numerous transformed cells can be monitored at the same time so that at least 400 transcription factors, at least 600 transcription factors and even at least 1000 transcription factors may be monitored simultaneously.

Following the initial screens a deconvolution method may be used to analyze the results of the above-mentioned experiments. Each experiment resulting in positive results is repeated, and positive repeat experiments are followed by deconvolution of the pools to a lower level of complexity. Transcription factor pools causing reporter activation may be deconvoluted to individual transcription factors. If no activation is observed when transcription factors are tested individually, pair-wise combinations of transcription factors are tested. The smallest set of transcription factors that produces gene activation is tested further.

A single promoter construct may tested in a screen or a promoter construct pool may be tested in a particular screen. If a promoter construct pool is employed, the promoter construct pool may be deconvoluted to individual promoter constructs.

Experiments resulting in the induction of a particular promoter:reporter gene construct may be repeated. Transcription factors that produce a consistent increase in target gene expression are processed further.

Depending on the ease of transformation of the secondary metabolite-producing species, different approaches are taken. If there is evidence that transformed cell suspension cultures of selected species can be generated efficiently, two different lines of analysis can be taken, depending on whether secondary metabolite accumulation can be measured reliably in cell suspension culture. If secondary metabolite accumulation can be measured reliably, cells are transformed, using transcription factors and control constructs. Secondary metabolite accumulation is then measured using standard analytical techniques, either in the medium or in cell extracts. If such measurements can be taken after transient gene expression, then this is the preferred approach, since it does not involve selecting for stable transformants. Otherwise, stable transformants are first generated.

The effects of transcription factors on the pathway may be evaluated at the level of pathway gene expression. Expression of selected pathway genes is compared in cell lines transformed with transcription factors and cells transformed with control constructs, using standard techniques such as Northern hybridization or RT-PCR. If multiple pathway genes are activated following overexpression of transcription factors, transgenic plants are generated and are tested for the accumulation of the desired secondary metabolites.

If transformation efficiency is low, it may be impractical to obtain transformed cell lines. Instead, promoters of previously untested secondary metabolite pathway genes can be isolated from the target species. These promoters can be fused to a reporter gene as described above, and tested in transient assays using the above-described methods. If multiple promoters are activated by the transcription factors that activated the first promoter tested, then one can confidently proceed to generating transgenic plants or cell lines using these transcription factors.

In certain embodiments, the transcription factors that produce a consistent increase in target gene expression are introduced into other species that produce the same secondary metabolite to confirm their effects. If secondary metabolite genes examined in this method are not endogenous to the species of cultured plant cell used for the assay, orthologs of the transcription factors which elevate metabolite pathway genes may also be later identified in other species. These orthologs can then be tested in their native species.

Generation of Stable Overexpressors

Once a transcription factor is identified useful for increasing expression form a pathway gene promoter, stable overexpressors may be generated by any method known to those of skill in the art, such as selection for antibiotic resistance. In a preferred embodiment, the highest expressors are identified by quantitation of mRNA. One of skill will recognize that after the expression cassette is stably incorporated in transgenic plants and confirmed to be operable, it can be introduced into other plants by sexual crossing. Any of a number of standard breeding techniques can be used, depending upon the species to be crossed. Secondary metabolites are extracted from flowers and leaves of plants or plant cell culture. Metabolites can be quantitated by any method known to those of skill in the art, such as GC-MS or HPLC (Satterwhite et al. *J Chromatogr.* 452:61–73 (1988)).

EXAMPLES

The following examples are offered to illustrate, but not to limit the present invention.

Example 1

Screen for Terpenoid Transcription Factors

The aim of this experiment was to discover transcription factors that regulate expression of terpenoid genes. In this experiment a pool of greater than 460 test transcription factors was examined. Some of the transcription factor members shared structural similarity to transcription factors known to be implicated in biosynthetic pathways. In other cases, the expression levels of the transcription factor gene members were known to be transcriptionally regulated in a similar fashion to the terpenoid pathway genes under investigation. Other transcription factor gene members were randomly selected.

Reporter constructs containing the taxadiene synthase and limonene synthase promoters, fused to an intron-interrupted uidA gene (intGUS), were constructed and expressed transiently in tobacco leaves, together with pools of transcription factor constructs. GUS activity of the transformed leaves was then measured, as an indication of terpenoid gene expression.

Terpenoid pr moter gene constructs were introduced into Agrobacterium cells. Suspensions of the resulting Agrobacteri m strains were then mixed with suspension of cells containing Arabidopsis transcription factor o erexpressor constructs prepared as described in U.S. pat. app. Ser. Nos. 09/394,519, filed Sep. 13, 1999, now abandoned, 09/506, 720, filed Feb. 17, 2000, now abandoned, 09/533,030, filed Mar. 22, 2000, now abandoned, 09/53 3,392, filed Mar. 22, 2000, now abandoned, 09/533,029, filed Mar. 22, 2000, vending, 09/532,591, filed Mar. 22, 2000, now abandoned, 09/533,648, filed Mar. 22, 2000, now abandoned, or PCT publications PCT/US00/31418, filed Nov. 14, 2000, now exoire PGT/US00/31458, filed Nov. 14, 2000, now exoired, PGTIUS00/31457 filed Nov. 14, 2000, ow expired, PCT/US00/31325, filed Nov. 14, 2000, now expired, PCT/US00/31414, filed Nov. 14, 2000, now expired, PGT/US00/31344, filed Nov. 14, 2000, now expired, and PCT/US00/28141. filed Oct. 11, 2000, now expired.

The resulting mixtures were infiltrated into leaves of *Nicotiana benthamiana* plants and GUS activity was measured 5 days after infiltration.

Cloning of the limonene synthase and taxadiene synthase promoters into intGUS containing binary vectors
Construction of a binary vector containing the int-GUS gene (p512)
A binary vector containing an enhanced 35S promoter, pMen065, was used as starting material. The int-GUS gene, which is the *E. Coli* uidA gene interrupted by an intron excised from a potato gene, was amplified using primers:

```
030418:                       (SEQ ID NO: 15)
CGCTCTAGACCGGAACCGTCGAGCATGGTCCGTCCTGTAG, and 030419:                       (SEQ ID NO: 16)
CGCGGATCCGCCAGGAGAGTTGTTGATTCATTGTTTGC.
```

IntGUS makes it possible to measure GUS activity in transformed plant samples without interference from GUS activity produced by Agrobacterium, where the gene is inactive. The PCR product as restricted using enzymes BamHI and XbaI, and cloned into the corresponding sites of pMen065, to produce plasmid p512.

Cloning of the taxadiene synthase (TDS) promoter into p512
The TDS promoter was PCR-amplified using primers:

```
030413:                       (SEQ IQ NO: 17)
ACCCAAGCTTGGGTGATATGACTTAAATATATGTACAAGTAGC and 030414:                       (SEQ ID NO: 18)
CGCGGATCCATTAATCTTTCCTTCCGCTCTCTTTCTATG.
```

The resulting PCR product was cut with BamHI and HindIII and cloned into the corresponding sites of pBluescript KS, to produce plasmid p528. P528, in turn, was cut with HindIII d NotI. p512 was restricted with the same enzymes, and the vector fragment was purified away from the 35S promoter fragment. The HindIII/NotI insert fragment from p528 was ligated to this vector fragment, producing plasmid p514.

Cloning of the limonene synthase (LS) promoter into p512

The LS promoter was PCR-amplified using primers:

```
021558:
GACCCAAGCTTGTTTGTTTTGACTAAGTTTGGGGGTGAG and

021559:
ACGCGGATCCGTAGAGAGGCAGTGAAACTACTGAAATTACG.
```

The same strategy as above was used to clone the LS promoter into pBluescript KS to produce p539. A HindIII/NotI fragment from p539 that contains the promoter was cloned into p512 as above, to generate plasmid p516.

Transformation of Agrobacterium cells with reporter constructs
Cells of nopaline Agrobacterium strain ABI were electroporated with binary vectors containing int-GUS fusion constructs. Transformed bacteria were selected on LB plates containing kanamycin (75 mg/l), spectinomycin (100 mg/l) and chloramphenicol (20 mg/l)

Infiltration of tobacco leaves using Agrobacterial cell suspensions
Bacterial growth
Agrobacterium cells were re-streaked onto selection plates a few days before infiltration. Overnight cultures were inoculated with Agrobacterium cells from these plates into 1 ml liquid selection media in deep-well 96-well plates. 85 ul of the overnight culture was added to 850 ul LB medium supplemented with 10 mM MES and 20 uM acetosyringone. The resulting culture was grown overnight to saturation (OD ~4). 450 ul of each transcription factor strain culture were combined to form pools of 4 transcription factor Agrobacterium strains. Agrobacterium pools were harvested by centrifugation (1500 g) and resuspended in 500 ul of an infiltration solution containing 10 mM MgC12, 10 mM MES and 150 uM acetosyringone, where they were incubated for a minimum of 2 hours at room temperature before infiltration. Each cell suspension was adjusted to an OD of 1. Reporter construct -containing strains were grown separately: an overnight 5 ml culture was used to inoculate a 50 ml culture, which was grown to saturation. Each strain was then resuspended in infiltration solution to a final OD of 1.

Infiltration
Promoter intGUS cell pools were produced by combining an equal volume of cell suspensions containing the limonene synthase and taxadiene synthase constructs. TF pools were mixed with an equal volume of promoter-intGUS pools. 100–300 ul of the mixture was infiltrated, into leaves of *Nicotiana benthamiana* plants, using a 1 ml syringe. Control suspensions were made up for one half of the reporter construct mix and, for the other half, of cells containing a binary vector without insert. Control infiltrations were performed in every leaf.

GUS activity in infiltrated leaves
5 days after infiltration, GUS activity of infiltrated tobacco leaves was measured using the following protocol. Leaf circles (~0.5 cm in diameter) were cut out of the infiltrated areas, using a cork borer. Two circles were transferred to each well of 96-well plates. 500 ul extraction buffer (50 mM NaHPO4 pH7.0, 10 mM 2-mercaptoethanol, 10 mM Na2EDTA) was added to each well. A metal ball was then placed in each well. The plates were capped tightly and placed in a paint shaker. After 20 min. shaking, sodium lauryl sarcosine and Triton X-100 were added to a final concentration of 0.1% v/v. The plates were vortexed gently and incubated for 10 min at room temperature, before centrifugation at 1,500 g for 20 min. 50 ul of supernatant were mixed with 250 ul of GUS assay solution (2 mM 4methylumbelliferyl-D-glucuronide in extraction buffer) and 200 ul of GUS extraction buffer. A 20–50 ul aliquot was removed immediately and added into 1 ml stop buffer (0.2 M sodium carbonate) to be used as control. The rest of the mixture was incubated at 37° C. for 60 min. 20–50 ul aliquots were added to stop buffer at the end of the period. GUS activity was determined by fluorometry.

Activation of expression from the taxadiene synthase gene promoter 117 transcription factor subpools consisting of 4 transcription factors each (a total of 464 transcription factors in the pool) were screened using the above method. Activation resulting in GUS activity increases larger than 1.5-fold was measured for 9 of these subpools. One of the transcription factor pools was deconvoluted to its individual transcription factor components, and the infiltration experiment was repeated for each reporter construct. One of the transcription factors in the pool (G872) was found to increase GUS activity an average 4-fold in plants co-infiltrated with the taxadiene synthase promoter construct. G872 is a member of the AP2 family and is shown as SEQ ID NOs: 7 and 8.

Activation of expression from the limonene synthase gene promoter 117 transcription factor subpools consisting of 4 transcription factors each ( a total of 464 transcription factors in the pool) were screened using the above method. Activation resulting in GUS activity increases larger than 1.5-fold was measured for 1 of these subpools. The transcription factor pool was deconvoluted to its individual transcription factor components, and the infiltration experiment was repeated for each reporter construct. One of the transcription factors in the pool (G1386) was found to increase GUS activity an average 2-fold in plants co-infiltrated with the limonene synthase promoter construct. G1386 is a member of the AP2 family and is shown as SEQ ID NOs: 5 and 6.

Example 2

Screen to Identify Synergistic Effects of Transcription Factors on the Taxadiene Synthase Gene As described in Example 1, reporter constructs containing the taxadiene synthase promoter fused to an intron-interrupted uidA gene (intGUS), were expressed transiently in tobacco, in subpools containing 4 transcription factor constructs. GUS activity of the transformed leaves was then measured as an indication of terpenoid gene expression.

One of the pools of four transcription factors consistently induced greater GUS induction—an average of 4.1 (figure is based on analysis of 10 infiltrated leaves×2 reps/leaf).

However, when the 4 transcription factors were deconvoluted, three of the transcription factors showed a low to moderate induction of pTDS when expressed alone and the fourth transcription factor showed no induction at all.

G993:1.3 fold
G1845:1.8 fold
G1386:2 fold

In addition we discovered that each of the pairwise combinations of the above genes gave a stronger induction than the individual genes alone. In two cases, the induction was as strong as that of the pool of four, thus indicating synergistic interactions between the two genes.

G993/G1386: 5-fold (pool of 4 control: 4.8-fold)
G993/G1845: 2.1 (pool of 4 control: 2.3)
G1386/G1845: 3.9 (pool of 4 control: 6.8)

Like the transcription factors identified in Example 1, G993 (SEQ ID NOs: 1 and 2), and G1845 (SEQ ID NOs: 3 and 4) are AP2 domain-containing transcription factors. And the degree of similarity between these genes and ORCA, a gene involved in terpenoid indole alkaloids biosynthesis (Plant J. 2001 January; 25(1):43-53), is only 50–60% in the AP2 domain and lower o the domain.

Example 3

Terpenoid Analysis in Plant Cell Culture

Species that produce terpenoids in suspension culture are identified. Suspension cultures may be established for species that produce either monoterpenes, sesquiterpenes or diterpenes. Different strains of Agrobacterium are tested for the transient expression of transgenes in suspension cells, and transformation efficiency is measured. Finally, if transformation is efficient enough, and terpenoid production is not induced by Agrobacterium infection alone in the absence of the transcription factor construct, every Arabidopsis transcription factor and selected combinations of transcription factors are transiently expressed in cultured cells to analyze increases in terpenoid biosynthesis. Appropriate elicitors of terpenoid production in culture may be used to enhance terpenoid yields.

Example 4

Terpenoid Analysis in Whole Plants

Terpenoids are extracted from Arabidopsis flowers and leaves of wild-type plants and analyzed by GC-MS, using protocols developed in-house for monoterpenes, and published protocols for sesqui and diterpenes. Headspace analysis is compared to extraction methods, and performed on leaves and flowers to characterize emitted volatile terpenoids. Basal terpenoid production levels are measured. In order to enhance terpenoid production, plants are submitted to treatments such as wounding and methyl-jasmonate application.

Arabidopsis overexpressors are grown and subjected to analysis to identify the best overexpressors for transcription factors that induce expression from the GUS reporter constructs. The 2 best overexpressing lines are analyzed for each of the transcription factors. For each line, T2 overexpressing plants are grown in appropriate numbers, together with control plants. Terpenoids are measured and related to fresh weight. The data are entered into a database. Any terpenoid phenotype is recorded and put in the context of other biochemical and non-biochemical phenotypes of overexpressing lines. Lines that produce significantly more terpenoids (more than twice the standard deviation of terpenoid accumulation in a wild-type population) are re-analyzed. If results agree between the two overexpressing lines, a third line is planted and analyzed. Only transcription factors for which consistent increases in terpenoid contents are observed are processed further.

Example 5

Detecting Expression of Genes in other Pathways

This example demonstrates that the method of this invention can be performed for other biological pathways, such as the dehydration stress-related pathway. The dehydration stress response is induced in conditions when plants experience cold, freezing, salt, or drought. As part of the pathway, metabolites such as sugars, proline, betaine, and the like are produced at increased levels. CBF3 is a transcription implicated in the pathway and activates expression of the rd29a gene (Yamaguchi-Shinozaki K Mol Gen Genet 1993 January;236(2–3):331–40 In this experiment we observed that transient transformation of the transcription factor CBF3 caused 12-fold activation of GUS expression from the rd29a:GUS construct. Stable overexpressors of CBF3 produce increased levels of sugar and proline compared with plants that do not overexpress CBF3.

A 910 bp BamHI/HindIII fragment from a cDNA clone containing the whole coding region of CBF3 (Gilmour et al., (1998) Plant J. 16,433–442) was inserted into the BglII and HindIII sites of the binary transformation vector pGA643. PGA643 has a CaMV 35S promoter and the terminator from gene 7 of pTiA6 (An, "Binary Vectors", Gynheung et al. eds (1988) *Plant Molecular Biology Manual,* Kluwer Acad. Publishers). The resulting plasmid, pMPS 13, which contains the CBF3 coding sequence under control of the CaMV 3 5S promoter, was transformed into *Agrobacterium tumefaciens* strain GV3101 by electroporation (Koncz et al. (1986) *Mol. Gen. Gen.* 204: 383). Arabidopsis plants were transformed with plasmid pMPS 13 or the transformation vector pGA643 using the floral dip method (Clough and Bent, (1998) *Plant J.* 16, 735–743). Transformed plants were selected on the basis of kanamycin resistance. Homozygous T3 or T4 plants were used in all experiments.

p511, the RD29A-intGUS construct, was prepared as follows. RD29A and intGUS PCR fragments were cloned in tandem into the vector pMEN65. The plasmid pMEN65 was restricted with the enzymes HindIII and BamHI, excising a fragment containing the 35S promoter. The main vector fragment was purified by gel electrophoresis. The RD29A and intGUS fragments were generated by the polymerase chain reaction (PCR). RD29A was amplified from 20 ng of *A. thaliana* genomic DNA in a 50 µL reaction with PFU Turbo DNA polymerase using the primers:

GCCCAAGCTTGGTTGCTATGGTAGGGACTAT and

TTTGATCCATGGTCCAAAGATTTTTTCTTTCCA.

The PCR product was purified with a Qiaquick PCR purification column, restricted with the enzymes HindIII and NcoI, and again purified with a Qiaquick PCR purification column. The intGUS sequence was amplified from 1 ng of the plasmid DNA pEGAD in a 50 µL reaction with PFU Turbo DNA polymerase using the primers AGCGCCATGGCCGGAACCGTCGAGCATGGTCCGTCCTGTAG and

CGCGGATCCGCCAGGAGAGTTGTTGATTCATTGTTTGC.

The PCR product was purified with a Qiaquick PCR purification column, restricted with the enzymes NcoI and BamHI, and again purified with a Qiaquick PCR purification column.

The three fragments were ligated together with a molar ratio of 1:2:2 (pMEN65:RD29A:intGUS) using T4 DNA ligase. The RD29A promoter will ligate upstream of the open reading frame of the intGUS gene. The ligation reaction was transformed into the *E. coli* DH5α and plasmid DNAs were isolated from resulting clones. Plasmid DNAs were sequenced across the HindIII and BamHI sites and through the RD29A and intGUS fragments to ensure that no mutations were introduced by PCR.

Example 6

Increased Production of Metabolites in Plants Overexpressing CBF3

After observing that transient transformation of the transcription factor CBF3 caused 12-fold activation of GUS expression from the rd29a:GUS construct, stable transformants were established and metabolite production levels were determined.

Lyophilized Arabidopsis leaf material (30 mg) was extracted with 3 ml deionized water at 80° C. for 15 min. The samples were shaken for approximately 1 hour at room temperature and then allowed to stand overnight at 4° C. The extracts were filtered through glass wool and analyzed for proline content using the acid ninhydrin reaction (Troll and Lindsley (1955) *J. Biol. Chem.* 215, 655–660). Proline levels in certain samples were confirmed by amino acid analysis using an amino acid analyzer at the Macromolecular Structure Facility in the Biochemistry Department at Michigan State University. The free proline levels in the CBF3-expressing plants were about 5-fold higher than they were in the control plants. The proline levels in the CBF3-expressing plants increased further (about 2-fold) upon cold acclimation and were 2–3 fold higher than those found in the cold-acclimated control plants.

Total soluble sugars (e.g. sucrose, glucose, and fructose among others) were extracted from lyophilized leaf material (20 mg) in 80% ethanol (2 ml) at 80° C. for 15 min. The samples were shaken for approximately 1 hr at room temperature and allowed to stand overnight at 4° C. Extracts were filtered through glass wool and chlorophyll removed by shaking samples (0.4 ml) with water (0.4 ml) and chloroform (0.4 ml). The aqueous extract was tested for sugar content using the phenol-sulfuric acid assay (Dubois et al., (1956) *Anal Chem.* 28, 350–356). Certain samples were dried down, suspended in water and the sugars analyzed by HPLC using a sugar column (Shodex, Shoko Co. Ltd., Japan) with a refractive index detector as previously described (Gao et al. (1999) *Physiol. Plant.* 106, 1–8). Retention times were compared to those of standard glucose, fructose and sucrose, and the peaks integrated using Millennium-32 software (Waters Corp.).

Our results show that CBF3 expression affected the sugar levels in plants. Total soluble sugars in control and CBF3-expressing plants at both nonacclimating and cold acclimating temperatures were measured. The results show that the levels of total sugars in nonacclimated CBF3-expressing plants were about 3-fold greater than those in nonacclimated control plants. Upon cold acclimation, sugar levels went up in both the control and CBF3-expressing plants about 2-fold, and remained about 3-fold higher in the CBF3-expressing plants. Analysis of the sugars by HPLC indicated that CBF3 expression affected the levels of sucrose; in nonacclimated control plants, sucrose levels were about 0.3 µg/100 µg dry weight (DW), while in nonacclimated CBF3-expressing plants they were about 1.5 µg/100 µg DW.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of determining whether a member of a pool of cloned test transcription factor polynucleotides encodes a plant pathway transcription factor, the method comprising: collecting a pool of cloned test transcription factor polynucleotides; introducing into a plant cell a nucleic acid comprising a plant promoter of a pathway gene operably linked to a reporter gene; introducing into the plant cell a member of the pool of cloned test transcription factor polynucleotides, wherein said member is selected on the basis of structural similarity to a known transcription factor for a pathway gene; and detecting expression of said reporter gene in the plant cell, thereby determining whether the member of the cloned test transcription factor polynucleotide pool encodes a plant pathway transcription factor.

2. The method of claim 1, further comprising detecting the expression of at least one other pathway gene in the cell.

3. The method of claim 1, wherein said cloned test transcription factor polynucleotide is from a plant.

4. The method of claim 1, wherein said cloned test transcription factor polynucleotide is expressed transiently in the plant cell.

5. The method of claim 1, wherein said plant promoter of a pathway gene operably linked to a reporter gene is transiently transfected into the plant cell.

6. The method of claim 1, wherein said reporter gene is beta-glucuronidase (GUS).

7. The method of claim 1, wherein said plant promoter of a pathway gene is the promoter of a biosynthetic pathway gene of a plant that produces secondary metabolites.

8. The method of claim 1, wherein said pathway gene is a biosynthetic pathway gene.

9. The method of claim 8, wherein said biosynthetic pathway gene is a primary metabolite pathway gene.

10. The method of claim 8, wherein said biosynthetic pathway gene is a secondary metabolite pathway gene.

11. The method of claim 10, wherein said secondary metabolite pathway gene is an alkaloid pathway gene.

12. The method of claim 10, wherein said secondary metabolite pathway gene is a terpenoid pathway gene.

13. The method of claim 12, wherein said terpenoid pathway gene is from a species selected from the group consisting of Mentha and Taxus.

14. The method of claim 12, wherein said terpenoid pathway gene is selected from the group consisting of limonene synthase and taxadiene synthase.

15. A method of determining whether a member of a pool of test transcription factor polynucleotides encodes a biosynthetic pathway transcription factor, comprising:

introducing into a plant cell nucleic acids comprising the test transcription factor polynucleotides and detecting expression of a biosynthetic pathway gene in the plant cell by quantitation of the biosynthetic pathway gene RNA level, wherein said member is selected on the basis of structural similarity to a known transcription factor for a pathway gene;

thereby determining whether the member of the cloned test transcription factor polynucleotide pool encodes a plant pathway transcription factor.

16. A method of determining whether two or more members of a pool of cloned test transcription factor polynucleotides are required for expression from a pathway gene promoter, wherein said two or more members of a pool of cloned test transcription factor polynucleotides are selected on the basis of structural similarity to a known transcription factor for a pathway gene, the method comprising:

collecting a pool of cloned test transcription factor polynucleotides;

introducing into plant cell a nucleic acid comprising a biosynthetic pathway gene promoter operably linked to a reporter gene;

introducing into plant cell the pool of cloned test transcription factor polynucleotides;

detecting expression from said biosynthetic pathway gene promoter in the plant cell, and deconvoluting the pool of cloned test transcription factor polynucleotides to identify the minimum number of cloned test transcription factor polynucleotides necessary to detect expression from said biosynthetic pathway gene promoter;

thereby determining whether two or more members of the cloned test transcription factor polynucleotide pool are required for expression from said biosynthetic pathway gene promoter.

17. The method of claim 16, further comprising detecting the expression of at least one other pathway gene in the cell.

18. The method of claim 16, wherein said biosynthetic pathway gene promoter is operably link to a biosynthetic pathway gene.

19. The method of claim 16, wherein said biosynthetic pathway gene promoter is a primary metabolite pathway gene promoter.

20. The method of claim 16, wherein said cloned test transcription factor polynucleotide is from a plant.

21. The method of claim 16, wherein said cloned test transcription factor polynucleotide is expressed transiently in the cell.

22. The method of claim 16, wherein said biosynthetic pathway gene promoter is the promoter of a biosynthetic pathway gene of a plant that produces secondary metabolites.

23. The method of claim 16, wherein said biosynthetic pathway gene promoter operably linked to a reporter gene is transiently transfected into a cell.

24. The method of claim 23, wherein said reporter gene is beta-glucuronidase (GUS).

25. The method of claim 16, wherein said biosynthetic pathway gene promoter is a secondary metabolite pathway gene promoter.

26. The method of claim 25, wherein said secondary metabolite pathway gene promoter is an alkaloid pathway gene promoter.

27. The method of claim 25, wherein said secondary metabolite pathway gene promoter is a terpenoid pathway gene promoter.

28. The method of claim 27, wherein said terpenoid pathway gene is from a species selected from the group consisting of Mentha and Taxus.

29. The method of claim 27, wherein said terpenoid pathway gene is selected from the group consisting of limonene synthase and taxadiene synthase.

* * * * *

SEQUENCE LISTING

```
<160> NUMBER OF SEQ ID NOS: 18

<210> SEQ ID NO 1
<211> LENGTH: 1239
<212> TYPE: DNA
<213> ORGANISM: Arabidopsis thaliana
<220> FEATURE:
<221> NAME/KEY: CDS
<222> LOCATION: (6)...(1091)
<223> OTHER INFORMATION: G993

<400> SEQUENCE: 1 caaat atg gaa tac agc tgt gta gac gac agt agt aca acg tca gaa tct      50
      Met Glu Tyr Ser Cys Val Asp Asp Ser Ser Thr Thr Ser Glu Ser
        1               5                  10                  15 ctc tcc atc tct act act cca aag ccg aca acg acg gag aag aaa            98
Leu Ser Ile Ser Thr Thr Pro Lys Pro Thr Thr Thr Glu Lys Lys
                20                  25                  30 ctc tct tct ccg ccg gcg acg tcg atg cgt ctc tac aga atg gga agc       146
Leu Ser Ser Pro Pro Ala Thr Ser Met Arg Leu Tyr Arg Met Gly Ser
            35                  40                  45 ggc gga agc agc gtc gtt ttg gat tca gag aac ggc gtc gag acc gag       194
Gly Gly Ser Ser Val Val Leu Asp Ser Glu Asn Gly Val Glu Thr Glu
        50                  55                  60 tca cgt aag ctt cct tcg tcg aaa tat aaa ggc gtt gtg cct cag cct       242
Ser Arg Lys Leu Pro Ser Ser Lys Tyr Lys Gly Val Val Pro Gln Pro
     65                  70                  75 aac gga aga tgg gga gct cag att tac gag aag cat cag cga gtt tgg       290
Asn Gly Arg Trp Gly Ala Gln Ile Tyr Glu Lys His Gln Arg Val Trp
 80                  85                  90                  95 ctc ggt act ttc aac gag gaa gaa gaa gct gcg tct tct tac gac atc       338
Leu Gly Thr Phe Asn Glu Glu Glu Glu Ala Ala Ser Ser Tyr Asp Ile
                100                 105                 110 gcc gtg agg aga ttc cgc ggc cgc gac gcc gtc act aac ttc aaa tct       386
Ala Val Arg Arg Phe Arg Gly Arg Asp Ala Val Thr Asn Phe Lys Ser
            115                 120                 125 caa gtt gat gga aac gac gcc gaa tcg gct ttt ctt gac gct cat tct       434
Gln Val Asp Gly Asn Asp Ala Glu Ser Ala Phe Leu Asp Ala His Ser
        130                 135                 140 aaa gct gag atc gtg gat atg ttg agg aaa cac act tac gcc gat gag       482
Lys Ala Glu Ile Val Asp Met Leu Arg Lys His Thr Tyr Ala Asp Glu
    145                 150                 155 ttt gag cag agt aga cgg aag ttt gtt aac ggc gac gga aaa cgc tct       530
Phe Glu Gln Ser Arg Arg Lys Phe Val Asn Gly Asp Gly Lys Arg Ser
160                 165                 170                 175 ggg ttg gag acg gcg acg tac gga aac gac gct gtt ttg aga gcg cgt       578
Gly Leu Glu Thr Ala Thr Tyr Gly Asn Asp Ala Val Leu Arg Ala Arg
                180                 185                 190 gag gtt ttg ttc gag aag act gtt acg ccg agc gac gtc ggg aag ctg       626
Glu Val Leu Phe Glu Lys Thr Val Thr Pro Ser Asp Val Gly Lys Leu
            195                 200                 205 aac cgt tta gtg ata ccg aaa caa cac gcg gag aag cat ttt ccg tta       674
```

```
Asn Arg Leu Val Ile Pro Lys Gln His Ala Glu Lys His Phe Pro Leu
        210                 215                 220 ccg gcg atg acg acg gcg atg ggg atg aat ccg tct ccg acg aaa ggc      722
Pro Ala Met Thr Thr Ala Met Gly Met Asn Pro Ser Pro Thr Lys Gly
        225                 230                 235 gtt ttg att aac ttg gaa gat aga aca ggg aaa gtg tgg cgg ttc cgt      770
Val Leu Ile Asn Leu Glu Asp Arg Thr Gly Lys Val Trp Arg Phe Arg
240                 245                 250                 255 tac agt tac tgg aac agc agt caa agt tac gtg ttg acc aag ggc tgg      818
Tyr Ser Tyr Trp Asn Ser Ser Gln Ser Tyr Val Leu Thr Lys Gly Trp
                260                 265                 270 agc cgg ttc gtt aaa gag aag aat ctt cga gcc ggt gat gtg gtt tgt      866
Ser Arg Phe Val Lys Glu Lys Asn Leu Arg Ala Gly Asp Val Val Cys
            275                 280                 285 ttc gag aga tca acc gga cca gac cgg caa ttg tat atc cac tgg aaa      914
Phe Glu Arg Ser Thr Gly Pro Asp Arg Gln Leu Tyr Ile His Trp Lys
        290                 295                 300 gtc cgg tct agt ccg gtt cag act gtg gtt agg cta ttc gga gtc aac      962
Val Arg Ser Ser Pro Val Gln Thr Val Val Arg Leu Phe Gly Val Asn
305                 310                 315 att ttc aat gtg agt aac gag aaa cca aac gac gtc gca gta gag tgt     1010
Ile Phe Asn Val Ser Asn Glu Lys Pro Asn Asp Val Ala Val Glu Cys
320                 325                 330                 335 gtt ggc aag aag aga tct cgg gaa gat gat ttg ttt tcg tta ggg tgt     1058
Val Gly Lys Lys Arg Ser Arg Glu Asp Asp Leu Phe Ser Leu Gly Cys
                340                 345                 350 tcc aag aag cag gcg att atc aac atc ttg tga caaattcttt ttttttggtt   1111
Ser Lys Lys Gln Ala Ile Ile Asn Ile Leu  *
            355                 360 ttttcttca atttgtttct ccttttcaa tatttgtat tgaaatgaca agttgtaaat      1171
taggacaaga caagaaaaaa tgacaactag acaaatagt ttttgtttaa aaaaaaaaaa    1231
aaaaaaaa                                                            1239

<210> SEQ ID NO 2
<211> LENGTH: 361
<212> TYPE: PRT
<213> ORGANISM: Arabidopsis thaliana

<400> SEQUENCE: 2

Met Glu Tyr Ser Cys Val Asp Asp Ser Ser Thr Thr Ser Glu Ser Leu
1               5                   10                  15

Ser Ile Ser Thr Thr Pro Lys Pro Thr Thr Thr Glu Lys Lys Leu
            20                  25                  30

Ser Ser Pro Pro Ala Thr Ser Met Arg Leu Tyr Arg Met Gly Ser Gly
        35                  40                  45

Gly Ser Ser Val Val Leu Asp Ser Glu Asn Gly Val Glu Thr Glu Ser
    50                  55                  60

Arg Lys Leu Pro Ser Ser Lys Tyr Lys Gly Val Val Pro Gln Pro Asn
65                  70                  75                  80

Gly Arg Trp Gly Ala Gln Ile Tyr Glu Lys His Gln Arg Val Trp Leu
                85                  90                  95

Gly Thr Phe Asn Glu Glu Glu Ala Ala Ser Ser Tyr Asp Ile Ala
            100                 105                 110

Val Arg Arg Phe Arg Gly Arg Asp Ala Val Thr Asn Phe Lys Ser Gln
        115                 120                 125

Val Asp Gly Asn Asp Ala Glu Ser Ala Phe Leu Asp Ala His Ser Lys
    130                 135                 140
```

```
Ala Glu Ile Val Asp Met Leu Arg Lys His Thr Tyr Ala Asp Glu Phe
145                 150                 155                 160

Glu Gln Ser Arg Arg Lys Phe Val Asn Gly Asp Gly Lys Arg Ser Gly
                165                 170                 175

Leu Glu Thr Ala Thr Tyr Gly Asn Asp Ala Val Leu Arg Ala Arg Glu
            180                 185                 190

Val Leu Phe Glu Lys Thr Val Thr Pro Ser Asp Val Gly Lys Leu Asn
        195                 200                 205

Arg Leu Val Ile Pro Lys Gln His Ala Glu Lys His Phe Pro Leu Pro
    210                 215                 220

Ala Met Thr Thr Ala Met Gly Met Asn Pro Ser Pro Thr Lys Gly Val
225                 230                 235                 240

Leu Ile Asn Leu Glu Asp Arg Thr Gly Lys Val Trp Arg Phe Arg Tyr
                245                 250                 255

Ser Tyr Trp Asn Ser Ser Gln Ser Tyr Val Leu Thr Lys Gly Trp Ser
            260                 265                 270

Arg Phe Val Lys Glu Lys Asn Leu Arg Ala Gly Asp Val Val Cys Phe
        275                 280                 285

Glu Arg Ser Thr Gly Pro Asp Arg Gln Leu Tyr Ile His Trp Lys Val
    290                 295                 300

Arg Ser Ser Pro Val Gln Thr Val Val Arg Leu Phe Gly Val Asn Ile
305                 310                 315                 320

Phe Asn Val Ser Asn Glu Lys Pro Asn Asp Val Ala Val Glu Cys Val
                325                 330                 335

Gly Lys Lys Arg Ser Arg Glu Asp Asp Leu Phe Ser Leu Gly Cys Ser
            340                 345                 350

Lys Lys Gln Ala Ile Ile Asn Ile Leu
        355                 360

<210> SEQ ID NO 3
<211> LENGTH: 1226
<212> TYPE: DNA
<213> ORGANISM: Arabidopsis thaliana
<220> FEATURE:
<221> NAME/KEY: CDS
<222> LOCATION: (111)...(989)
<223> OTHER INFORMATION: G1845

<400> SEQUENCE: 3
aagacataat tttctctgtt ttcctagctc tctcctctca aattcttcca ttgctctctg    60
ttttggcaaa tcgtgaactg ccacgtcttt aaggcatcag tgaagcaaag atg gac     116
                                                        Met Asp
                                                          1 ttt gac gag gag cta aat ctt tgt att acg aaa ggt aaa aat gtt gat   164
Phe Asp Glu Glu Leu Asn Leu Cys Ile Thr Lys Gly Lys Asn Val Asp
        5                  10                  15 cat tct ttt gga gga gaa gct tct tcc acg tcc cca aga tct atg aag   212
His Ser Phe Gly Gly Glu Ala Ser Ser Thr Ser Pro Arg Ser Met Lys
 20                  25                  30 aaa atg aag agt cct agt cgt cct aaa ccc tat ttc caa tcc tct tct   260
Lys Met Lys Ser Pro Ser Arg Pro Lys Pro Tyr Phe Gln Ser Ser Ser
 35                  40                  45                  50 tct cct tat tcg tta gag gct ttc cct ttt tct ctc gat cca aca ctt   308
Ser Pro Tyr Ser Leu Glu Ala Phe Pro Phe Ser Leu Asp Pro Thr Leu
             55                  60                  65 cag aat cag caa caa caa ctc gga tca tac gtt ccg gta ctt gag caa   356
Gln Asn Gln Gln Gln Gln Leu Gly Ser Tyr Val Pro Val Leu Glu Gln
```

|  |  |  |  |  |  |  |  |  |  |  |  |  |  |  |  |
|---|---|---|---|---|---|---|---|---|---|---|---|---|---|---|---|
|  |  | 70 |  |  |  |  | 75 |  |  |  |  | 80 |  |  |  |
| cga | caa | gac | ccg | aca | atg | caa | ggc | cag | aag | caa | atg | atc | tcc | ttt | agt | 404 |
| Arg | Gln | Asp | Pro | Thr | Met | Gln | Gly | Gln | Lys | Gln | Met | Ile | Ser | Phe | Ser |  |
|  |  | 85 |  |  |  |  | 90 |  |  |  |  | 95 |  |  |  |  |

```
cct caa caa caa caa cag cag cag cag tat atg gcc cag tac tgg agt      452
Pro Gln Gln Gln Gln Gln Gln Gln Gln Tyr Met Ala Gln Tyr Trp Ser
        100                 105                 110 gac aca ttg aat ctg agt cca aga gga aga atg atg atg atg atg agc      500
Asp Thr Leu Asn Leu Ser Pro Arg Gly Arg Met Met Met Met Met Ser
115                 120                 125                 130 caa gaa gct gtt caa cct tac atc gca acg aag ctg tac aga gga gtg      548
Gln Glu Ala Val Gln Pro Tyr Ile Ala Thr Lys Leu Tyr Arg Gly Val
                135                 140                 145 aga caa cgt caa tgg gga aaa tgg gtc gca gag atc cgt aag cca cga      596
Arg Gln Arg Gln Trp Gly Lys Trp Val Ala Glu Ile Arg Lys Pro Arg
            150                 155                 160 agc agg gca cgt ctt tgg ctt ggt acc ttt gat aca gct gaa gaa gct      644
Ser Arg Ala Arg Leu Trp Leu Gly Thr Phe Asp Thr Ala Glu Glu Ala
        165                 170                 175 gcc atg gcc tac gac cgc caa gcc ttc aaa tta cga ggc cac agc gca      692
Ala Met Ala Tyr Asp Arg Gln Ala Phe Lys Leu Arg Gly His Ser Ala
    180                 185                 190 aca ctg aat ttc ccg gag cat ttt gtg aat aag gaa agc gag ctg cat      740
Thr Leu Asn Phe Pro Glu His Phe Val Asn Lys Glu Ser Glu Leu His
195                 200                 205                 210 gat tca aac tcg tcg gat cag aaa gaa cct gaa acg cca cag cca agc      788
Asp Ser Asn Ser Ser Asp Gln Lys Glu Pro Glu Thr Pro Gln Pro Ser
                215                 220                 225 gag gtt aac ttg gag agc aag gaa cta ccg gtg att gat gtt ggg aga      836
Glu Val Asn Leu Glu Ser Lys Glu Leu Pro Val Ile Asp Val Gly Arg
            230                 235                 240 gag gaa ggt atg gct gag gca tgg tac aat gcc att aca tcg gga tgg      884
Glu Glu Gly Met Ala Glu Ala Trp Tyr Asn Ala Ile Thr Ser Gly Trp
        245                 250                 255 ggt cct gaa agt cct ctt tgg gat gat ttg gat agt tct cat cag ttt      932
Gly Pro Glu Ser Pro Leu Trp Asp Asp Leu Asp Ser Ser His Gln Phe
    260                 265                 270 tca tca gaa agc tca tct tct tct cct ctc tct tgt cct atg agg cct      980
Ser Ser Glu Ser Ser Ser Ser Pro Leu Ser Cys Pro Met Arg Pro
275                 280                 285                 290 ttc ttt tga aaagtttat aaacccacat tgtgttgtag gttatagttt              1029
Phe Phe  * agggttatgc tcattggcat ttggatggag gcaattttg tgatctccca ttccaccaca    1089
tatcagtcat tatatgtgtc tacctttct ctgtatttct atcattatca ttgttttat     1149 tatgtgtctg tatgtgtttc cctattgcta catacataga tgtcctcttt gttcaaaaaa   1209
aaaaaaaaaa aaaaaaa                                                  1226

<210> SEQ ID NO 4
<211> LENGTH: 292
<212> TYPE: PRT
<213> ORGANISM: Arabidopsis thaliana

<400> SEQUENCE: 4

Met Asp Phe Asp Glu Glu Leu Asn Leu Cys Ile Thr Lys Gly Lys Asn
 1               5                  10                  15

Val Asp His Ser Phe Gly Gly Glu Ala Ser Ser Thr Ser Pro Arg Ser
            20                  25                  30
```

-continued

```
Met Lys Lys Met Lys Ser Pro Ser Arg Pro Lys Pro Tyr Phe Gln Ser
            35                  40                  45

Ser Ser Ser Pro Tyr Ser Leu Glu Ala Phe Pro Phe Ser Leu Asp Pro
    50                  55                  60

Thr Leu Gln Asn Gln Gln Gln Leu Gly Ser Tyr Val Pro Val Leu
65                  70                  75                  80

Glu Gln Arg Gln Asp Pro Thr Met Gln Gly Lys Gln Met Ile Ser
                85                  90                  95

Phe Ser Pro Gln Gln Gln Gln Gln Gln Tyr Met Ala Gln Tyr
            100                 105                 110

Trp Ser Asp Thr Leu Asn Leu Ser Pro Arg Gly Arg Met Met Met
            115                 120                 125

Met Ser Gln Glu Ala Val Gln Pro Tyr Ile Ala Thr Lys Leu Tyr Arg
    130                 135                 140

Gly Val Arg Gln Arg Gln Trp Gly Lys Trp Val Ala Glu Ile Arg Lys
145                 150                 155                 160

Pro Arg Ser Arg Ala Arg Leu Trp Leu Gly Thr Phe Asp Thr Ala Glu
                165                 170                 175

Glu Ala Ala Met Ala Tyr Asp Arg Gln Ala Phe Lys Leu Arg Gly His
            180                 185                 190

Ser Ala Thr Leu Asn Phe Pro Glu His Phe Val Asn Lys Glu Ser Glu
    195                 200                 205

Leu His Asp Ser Asn Ser Ser Asp Gln Lys Glu Pro Glu Thr Pro Gln
His 210                 215                 220

Pro Ser Glu Val Asn Leu Glu Ser Lys Glu Leu Pro Val Ile Asp Val
225                 230                 235                 240

Gly Arg Glu Glu Gly Met Ala Glu Ala Trp Tyr Asn Ala Ile Thr Ser
                245                 250                 255

Gly Trp Gly Pro Glu Ser Pro Leu Trp Asp Asp Leu Asp Ser Ser His
            260                 265                 270

Gln Phe Ser Ser Glu Ser Ser Ser Ser Pro Leu Ser Cys Pro Met
    275                 280                 285

Arg Pro Phe Phe
    290
```

<210> SEQ ID NO 5
<211> LENGTH: 845
<212> TYPE: DNA
<213> ORGANISM: Arabidopsis thaliana
<220> FEATURE:
<221> NAME/KEY: CDS
<222> LOCATION: (89)...(673)
<223> OTHER INFORMATION: G1386

<400> SEQUENCE: 5

```
aattttattt ccttctctca aatcttccca ccaaaaatta actctttcgt tcacactaag      60
tcccttttaa aagaaaatat cccaatta atg gaa cgt gac gac tgc cgg aga        112
                              Met Glu Arg Asp Asp Cys Arg Arg
                                1               5 ttt cag gac tcg ccg gcg cag acg acg gag aga aga gtg aaa tat aaa      160
Phe Gln Asp Ser Pro Ala Gln Thr Thr Glu Arg Arg Val Lys Tyr Lys
        10                  15                  20 cca aag aag aaa aga gcc aaa gat gat gat gat gag aaa gtt gtt tcg      208
Pro Lys Lys Lys Arg Ala Lys Asp Asp Asp Asp Glu Lys Val Val Ser
 25                  30                  35                  40 aag cat cca aat ttt cga ggt gtc aga atg aga caa tgg gga aaa tgg      256
Lys His Pro Asn Phe Arg Gly Val Arg Met Arg Gln Trp Gly Lys Trp
```

-continued

```
                    45                  50                  55
gtg tcc gaa atc aga gag cca aaa aag aaa tca aga atc tgg ctc ggt        304
Val Ser Glu Ile Arg Glu Pro Lys Lys Lys Ser Arg Ile Trp Leu Gly
                60                  65                  70 act ttc tcc acg gcg gag atg gcg gcg cgt gct cac gac gtg gca gct        352
Thr Phe Ser Thr Ala Glu Met Ala Ala Arg Ala His Asp Val Ala Ala
        75                  80                  85 tta gcc atc aaa ggc ggt tct gca cat ctc aac ttc ccg gag ctc gct        400
Leu Ala Ile Lys Gly Gly Ser Ala His Leu Asn Phe Pro Glu Leu Ala
    90                  95                 100 tat cac ctc cct aga cca gct agt gcc gac cct aaa gac atc caa gct        448
Tyr His Leu Pro Arg Pro Ala Ser Ala Asp Pro Lys Asp Ile Gln Ala
105                 110                 115                 120 gcc gcc gcc gca gct gca gcc gct gtg gcc att gac atg gat gta gag        496
Ala Ala Ala Ala Ala Ala Ala Val Ala Ile Asp Met Asp Val Glu
                125                 130                 135 acg tct tcg ccg tcg cca tct ccc aca gtt acg gaa acg tca tct ccg        544
Thr Ser Ser Pro Ser Pro Ser Pro Thr Val Thr Glu Thr Ser Ser Pro
                140                 145                 150 gct atg ata gca ctc tcc gac gac gcg ttc tcc gat ctt cct gat ctc        592
Ala Met Ile Ala Leu Ser Asp Asp Ala Phe Ser Asp Leu Pro Asp Leu
            155                 160                 165 ttg ctc aac gtg aac cat aac atc gat ggc ttc tgg gac tct ttt ccc        640
Leu Leu Asn Val Asn His Asn Ile Asp Gly Phe Trp Asp Ser Phe Pro
    170                 175                 180 tat gaa gaa ccc ttc ctc tct caa agt tac tag aaactcaaaa ctatgtcgtt      693
Tyr Glu Glu Pro Phe Leu Ser Gln Ser Tyr *
185                 190 tttgtatgta tttttgtcat gtgaccattt tttgacgtcg aaaatcaccc ggataatcca      753
aattgtatga tttattaatg gttgatgatt ttctttgtgt ggaacaatgt gtatgatacg      813
taatcaaaag ttcaaaaaaa aaataaaaaa aa                                    845

<210> SEQ ID NO 6
<211> LENGTH: 194
<212> TYPE: PRT
<213> ORGANISM: Arabidopsis thaliana

<400> SEQUENCE: 6

Met Glu Arg Asp Asp Cys Arg Arg Phe Gln Asp Ser Pro Ala Gln Thr
  1               5                  10                  15

Thr Glu Arg Arg Val Lys Tyr Lys Pro Lys Lys Arg Ala Lys Asp
            20                  25                  30

Asp Asp Asp Glu Lys Val Val Ser Lys His Pro Asn Phe Arg Gly Val
        35                  40                  45

Arg Met Arg Gln Trp Gly Lys Trp Val Ser Glu Ile Arg Glu Pro Lys
    50                  55                  60

Lys Lys Ser Arg Ile Trp Leu Gly Thr Phe Ser Thr Ala Glu Met Ala
65                  70                  75                  80

Ala Arg Ala His Asp Val Ala Ala Leu Ala Ile Lys Gly Gly Ser Ala
                85                  90                  95

His Leu Asn Phe Pro Glu Leu Ala Tyr His Leu Pro Arg Pro Ala Ser
            100                 105                 110

Ala Asp Pro Lys Asp Ile Gln Ala Ala Ala Ala Ala Ala Ala Ala Ala
        115                 120                 125

Val Ala Ile Asp Met Asp Val Glu Thr Ser Ser Pro Ser Pro Ser Pro
    130                 135                 140
```

```
Thr Val Thr Glu Thr Ser Ser Pro Ala Met Ile Ala Leu Ser Asp Asp
145                 150                 155                 160

Ala Phe Ser Asp Leu Pro Asp Leu Leu Leu Asn Val Asn His Asn Ile
            165                 170                 175

Asp Gly Phe Trp Asp Ser Phe Pro Tyr Glu Glu Pro Phe Leu Ser Gln
        180                 185                 190

Ser Tyr

<210> SEQ ID NO 7
<211> LENGTH: 891
<212> TYPE: DNA
<213> ORGANISM: Arabidopsis thaliana
<220> FEATURE:
<221> NAME/KEY: CDS
<222> LOCATION: (59)...(646)
<223> OTHER INFORMATION: G872

<400> SEQUENCE: 7
ccggaaacag aatccaattc aaccaaaccg aatcgaaccg aaccggagtt tttatcca          58 atg gtg aag caa gcg atg aag gaa gag gag aag aag aga aac acg gcg        106
Met Val Lys Gln Ala Met Lys Glu Glu Glu Lys Lys Arg Asn Thr Ala
 1               5                  10                  15 atg cag tca aag tac aaa gga gtg agg aag agg aaa tgg gga aaa tgg        154
Met Gln Ser Lys Tyr Lys Gly Val Arg Lys Arg Lys Trp Gly Lys Trp
                20                  25                  30 gta tcg gag atc aga ctt cca cac agc aga gaa cga att tgg tta ggc        202
Val Ser Glu Ile Arg Leu Pro His Ser Arg Glu Arg Ile Trp Leu Gly
            35                  40                  45 tct tac gac act ccc gag aag gcg gcg cgt gct ttc gac gcc gct caa        250
Ser Tyr Asp Thr Pro Glu Lys Ala Ala Arg Ala Phe Asp Ala Ala Gln
        50                  55                  60 ttt tgt ctc cgc ggc ggc gat gct aat ttc aat ttc cct aat aat cca        298
Phe Cys Leu Arg Gly Gly Asp Ala Asn Phe Asn Phe Pro Asn Asn Pro
 65                  70                  75                  80 ccg tcg atc tcc gta gaa aag tcg ttg acg cct ccg gag att cag gaa        346
Pro Ser Ile Ser Val Glu Lys Ser Leu Thr Pro Pro Glu Ile Gln Glu
                 85                  90                  95 gct gct gct aga ttc gct aac aca ttc caa gac att gtc aag gga gaa        394
Ala Ala Ala Arg Phe Ala Asn Thr Phe Gln Asp Ile Val Lys Gly Glu
            100                 105                 110 gaa gaa tcg ggt tta gta ccc gga tcc gag atc cga cca gag tct cct        442
Glu Glu Ser Gly Leu Val Pro Gly Ser Glu Ile Arg Pro Glu Ser Pro
        115                 120                 125 tct aca tct gca tct gtt gct aca tcg acg gtg gat tat gat ttt tcg        490
Ser Thr Ser Ala Ser Val Ala Thr Ser Thr Val Asp Tyr Asp Phe Ser
130                 135                 140 ttt ttg gat ttg ctt ccg atg aat ttc ggg ttt gat tcc ttc tcc gac        538
Phe Leu Asp Leu Leu Pro Met Asn Phe Gly Phe Asp Ser Phe Ser Asp
145                 150                 155                 160 gac ttc tct ggc ttc tcc ggt ggt gat cga ttt aca gag att tta ccc        586
Asp Phe Ser Gly Phe Ser Gly Gly Asp Arg Phe Thr Glu Ile Leu Pro
            165                 170                 175 atc gaa gat tac gga gga gag agt tta tta gat gaa tct ttg att ctt        634
Ile Glu Asp Tyr Gly Gly Glu Ser Leu Leu Asp Glu Ser Leu Ile Leu
        180                 185                 190 tgg gat ttt tga attcccaaac ataatatttt tttagagcga actgtgagat            686
Trp Asp Phe *
        195 tttccttgga gtcatggaga aatctggaga ttttttgtaa cacggagctc caatgacccg      746
```

-continued

```
ggaatttctt tcgtttcgga tccgaatttg atgtggatca tattcacacc tatatttttt      806 cattttttg ttgtaaagaa aaatcggata agattctagt aataaatgtt aaaagtccat       866
ttcattaaaa aaaaaaaaaa aaaaa                                            891
```

<210> SEQ ID NO 8
<211> LENGTH: 195
<212> TYPE: PRT
<213> ORGANISM: Arabidopsis thaliana

<400> SEQUENCE: 8

```
Met Val Lys Gln Ala Met Lys Glu Glu Lys Lys Arg Asn Thr Ala
 1               5                  10                  15

Met Gln Ser Lys Tyr Lys Gly Val Arg Lys Arg Lys Trp Gly Lys Trp
            20                  25                  30

Val Ser Glu Ile Arg Leu Pro His Ser Arg Glu Arg Ile Trp Leu Gly
        35                  40                  45

Ser Tyr Asp Thr Pro Glu Lys Ala Ala Arg Ala Phe Asp Ala Ala Gln
    50                  55                  60

Phe Cys Leu Arg Gly Gly Asp Ala Asn Phe Asn Phe Pro Asn Asn Pro
65                  70                  75                  80

Pro Ser Ile Ser Val Glu Lys Ser Leu Thr Pro Pro Glu Ile Gln Glu
                85                  90                  95

Ala Ala Ala Arg Phe Ala Asn Thr Phe Gln Asp Ile Val Lys Gly Glu
            100                 105                 110

Glu Glu Ser Gly Leu Val Pro Gly Ser Glu Ile Arg Pro Glu Ser Pro
        115                 120                 125

Ser Thr Ser Ala Ser Val Ala Thr Ser Thr Val Asp Tyr Asp Phe Ser
    130                 135                 140

Phe Leu Asp Leu Leu Pro Met Asn Phe Gly Phe Asp Ser Phe Ser Asp
145                 150                 155                 160

Asp Phe Ser Gly Phe Ser Gly Gly Asp Arg Phe Thr Glu Ile Leu Pro
                165                 170                 175

Ile Glu Asp Tyr Gly Gly Glu Ser Leu Leu Asp Glu Ser Leu Ile Leu
            180                 185                 190

Trp Asp Phe
        195
```

<210> SEQ ID NO 9
<211> LENGTH: 39
<212> TYPE: DNA
<213> ORGANISM: Artificial Sequence
<220> FEATURE:
<223> OTHER INFORMATION: PCR primer

<400> SEQUENCE: 9

```
gacccaagct tgtttgtttt gactaagttt gggggtgag                              39
```

<210> SEQ ID NO 10
<211> LENGTH: 41
<212> TYPE: DNA
<213> ORGANISM: Artificial Sequence
<220> FEATURE:
<223> OTHER INFORMATION: PCR primer

<400> SEQUENCE: 10

```
acgcggatcc gtagagaggc agtgaaacta ctgaaattac g                           41
```

<210> SEQ ID NO 11

```
<211> LENGTH: 31
<212> TYPE: DNA
<213> ORGANISM: Artificial Sequence
<220> FEATURE:
<223> OTHER INFORMATION: PCR primer

<400> SEQUENCE: 11
gcccaagctt ggttgctatg gtagggacta t                              31

<210> SEQ ID NO 12
<211> LENGTH: 34
<212> TYPE: DNA
<213> ORGANISM: Artificial Sequence
<220> FEATURE:
<223> OTHER INFORMATION: PCR primer

<400> SEQUENCE: 12
tttgatccat ggtccaaaga tttttttctt tcca                           34

<210> SEQ ID NO 13
<211> LENGTH: 41
<212> TYPE: DNA
<213> ORGANISM: Artificial Sequence
<220> FEATURE:
<223> OTHER INFORMATION: PCR primer

<400> SEQUENCE: 13
agcgccatgg ccggaaccgt cgagcatggt ccgtcctgta g                   41

<210> SEQ ID NO 14
<211> LENGTH: 38
<212> TYPE: DNA
<213> ORGANISM: Artificial Sequence
<220> FEATURE:
<223> OTHER INFORMATION: PCR primer

<400> SEQUENCE: 14
cgcggatccg ccaggagagt tgttgattca ttgtttgc                       38

<210> SEQ ID NO 15
<211> LENGTH: 40
<212> TYPE: DNA
<213> ORGANISM: Artificial Sequence
<220> FEATURE:
<223> OTHER INFORMATION: PCR primer

<400> SEQUENCE: 15
cgctctagac cggaaccgtc gagcatggtc cgtcctgtag                     40

<210> SEQ ID NO 16
<211> LENGTH: 38
<212> TYPE: DNA
<213> ORGANISM: Artificial Sequence
<220> FEATURE:
<223> OTHER INFORMATION: PCR primer

<400> SEQUENCE: 16
cgcggatccg ccaggagagt tgttgattca ttgtttgc                       38

<210> SEQ ID NO 17
<211> LENGTH: 43
<212> TYPE: DNA
<213> ORGANISM: Artificial Sequence
<220> FEATURE:
<223> OTHER INFORMATION: PCR primer

<400> SEQUENCE: 17
```

```
                                    -continued acccaagctt gggtgatatg acttaaatat atgtacaagt agc                       43

<210> SEQ ID NO 18
<211> LENGTH: 39
<212> TYPE: DNA
<213> ORGANISM: Artificial Sequence
<220> FEATURE:
<223> OTHER INFORMATION: PCR primer

<400> SEQUENCE: 18
cgcggatcca ttaatctttc cttccgctct ctttctatg                            39
```